July 16, 1968 A. D. MABS Plant Pat. 2,818
NAVEL ORANGE TREE
Filed Sept. 12, 1966
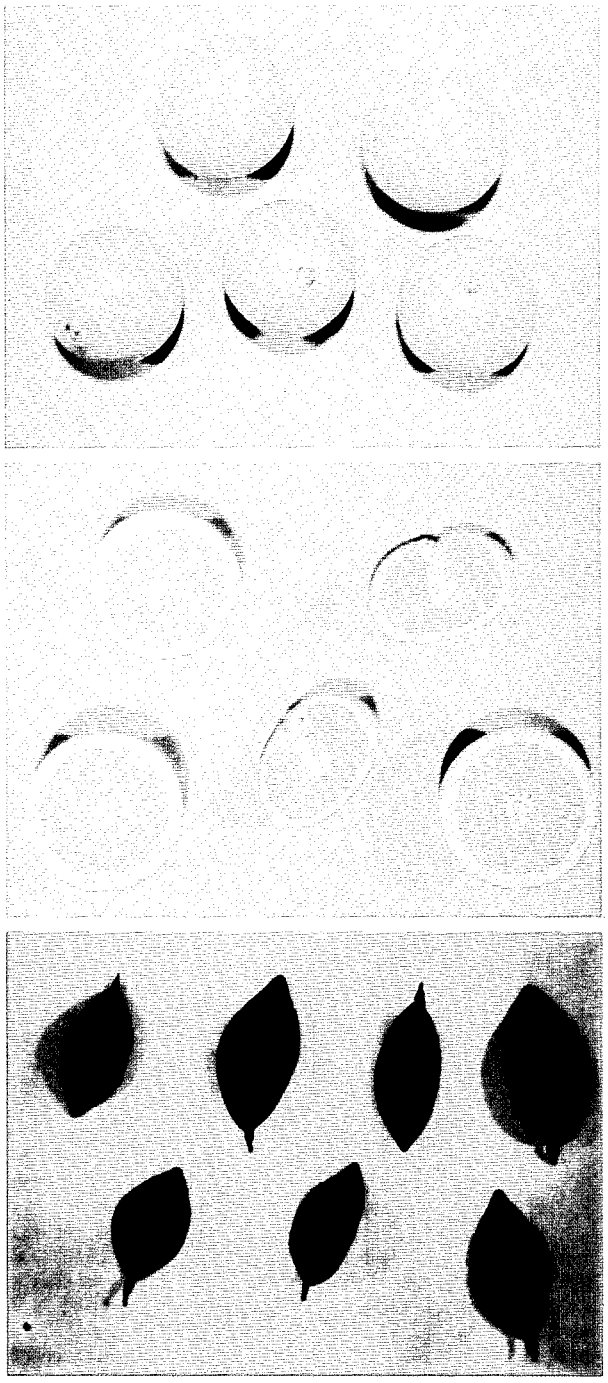
Inventor.
Arthur D. Mabs
By: Robb & Robb
Attorneys.

United States Patent Office

Plant Pat. 2,818
Patented July 16, 1968

2,818

NAVEL ORANGE TREE

Arthur D. Mabs, Strathmore, Calif., assignor to Central Valley MM Farms, Strathmore, Calif., a partnership

Filed Sept. 12, 1966, Ser. No. 578,897
1 Claim. (Cl. Plt.—45)

The present invention relates to a new and distinct variety of navel orange tree which was discovered by me as a limb sport of the variety known as Washington Navel orange (unpatented), in an orange grove on my property located near Porterville, in the county of Tulare, State of California.

At the time of my initial discovery of the sport referred to above, I was growing a grove of Washington Navel orange trees on my property aforesaid, and my attention was attracted to a limb on one tree of the Washington Navel orange variety which bore fruit that were highly colored much earlier than the other fruit on the same tree, as well as earlier than the coloring of the fruit on all of the other Washington Navel orange trees in the grove. Close inspection of the particular tree referred to showed that it had sported, and I thereupon carefully preserved the sport limb and propagated the sport by budding, as performed by me on my aforementioned property near Porterville. Continued observations of the sport limb and the progeny derived therefrom, together with extensive field and laboratory tests, fully confirmed the early coloring habit of the new sport along with other important features, representing a new variety, as evidenced by the following unique combination of characteristics which are outstanding therein, and which distinguish it from its parent, as well as from all other navel orange varieties of which I am aware:

(1) Foliage which is somewhat smaller than that of the Washington Navel parent;

(2) A habit of blooming profusely and setting fruit exceptionally well at an early age, usually beginning at one or two years of age when grown in the field, as distinguished from the usual third or fourth year required for consistent bearing performance of old-line Washington Navel varieties, and which is not affected by cultural practices or differences in rootstocks;

(3) Stout fruit stems which cause the fruit to remain more firmly attached to the tree than in the Washington Navel parent;

(4) Rapid acceleration of the growth of the small fruit which usually becomes apparent during the month of May and early June in California, as hereinafter more particularly described;

(5) A habit of changing the fruit color from green to orange more rapidly than the Washington Navel parent, as indicated by the fact that on October 25, the color of the fruit of my new variety was Aniline Yellow when that of the parent variety was Spinach Green, while on November 10, the new variety was Mikado Orange and the parent fruit was Aniline Yellow, and on November 25, the new variety was Orange Chrome and the parent fruit was Capucine Yellow;

(6) A fruit maturity ranging from 10 days to 3 weeks earlier than the Washington Navel variety in reaching the required sugar or soluble solids to acid ratio of 8:1;

(7) Excellent quality and flavor of the fruit comparable to the parent variety.

The accompanying drawing shows typical specimens of the foliage and fruit of my new variety with some of the fruit specimens being shown in both axial and transverse cross-section to depict the interior details thereof, all as illustrated in color as nearly true as it is reasonably possible to make the same in a color illustration of this character.

The following is a detailed description of my new navel orange variety, with color terminology in accordance with Ridgeway's Color Standards and Nomenclature, except where ordinary color terms of dictionary significance are obvious, said description being based upon observations made at Porterville and also at Chowchilla, in Madera County, Calif.

Dates of first and last pickings: About October 27 and January 15, respectively, at least 2 weeks earlier than other navel varieties grown under the same conditions in California.

Tree: Medium size; vigorous; drooping; productive.

*Trunk.*—Medium stockiness.

*Branches.*—Medium stockiness; angular branchlets; spines slender, stiff and ranging from large to small size; new wood medium vigorous.

*Leaves.*—Medium thickness; unifoliate; crenate; sharply pointed; few glands; petioles not widely winged; from about 2½ inches to 3 inches long and from about ¼ inch to 1 9/16 inches wide, as distinguished from the larger leaf size of the parent variety which ranges from about 3½ inches to 4 1/16 inches long and from about 1½ inches to 1⅝ inches wide. Color: upper surface—dark green; under surface—light green.

Flowers:

*Normal blooming period.*—Begins about one week ahead of Washington Navel.

*Borne.*—In clusters.

Fruit:

*Size.*—Variable. Circumference—about 10¾ inches. Axial diameter—about 3 3/16 inches. Transverse diameter—about 3 inches.

*Form.*—Uniform; unsymmetrical; globose; obovoid.

*Base.*—Depressed; furrowed,

*Apex.*—Depressed.

*Navel.*—Small; open; sometimes depressed and sometimes protruding.

*Stem.*—Size—medium stoutness. Position—straight. Color—light green.

*Calyx.*—Raised. Segments—5 in number; obtuse.

*Rind.*—Free and close early in season; surface pebbled; from about 3/16 inch to 5/16 inch thick.

*Flavor.*—Similar to Washington Navel.

*Color.*—From Deep Chrome, Plate II to Cadmium, Plate III.

*Bloom.*—Abundant.

*Oil cells.*—Medium size; even.

*Segments.*—Usually 12 or 13 in number. Size—uniform and separate easily. Dorsal surface—rounded. Walls—thin; firm to touch.

*Flesh.*—Color—from Light Cadmium to orange. Texture—medium; tender. Rag in flesh—slight. Vesicles—long; fusiform. Juice—abundant; evenly distributed in section. Flavor—delicate; well blended. Quality—good.

*Seeds.*—Seedless.

Keeping quality: Good.

Shipping quality: Good.

Resistance to insects and diseases: Medium resistance to the usual insects and disease to which navel orange are normally subject, as determined by comparison with other varieties grown under the same conditions in California.

General observations: The maturity development of my new navel orange variety is shown by the following tables:

TABLE I.—SOLUBLE SOLIDS TO ACID RATIO OF NEW VARIETY

| Date | New Var. on Cleopatra Mandarin Rootstock | New Var. on Troyer Citrange Rootstock | New Var. on Trifoliate Rootstock | Frost Nucellar on Trifoliate | Atwood on Cleopatra |
|---|---|---|---|---|---|
| 10/16 | 6.3:1 | 7.0:1 | 6.9:1 | 6.0:1 | 5.8:1 |
| 10/30 | 9.1:1 | 8.9:1 | 7.6:1 | 6.6:1 | 7.8:1 |
| 11/13 | 8.9:1 | 8.9:1 | 8.9:1 | 8.2:1 | 7.3:1 |
| 11/26 | 10.0:1 | 9.7:1 | 9.2:1 | 8.9:1 | 8.9:1 |
| 12/10 | 11.2:1 | 9.6:1 | 9.5:1 | 9.1:1 | 9.3:1 |
| 12/31 | 10.7:1 | 11.7:1 | 11.2:1 | 9.8:1 | ---------- |

TABLE II.—ACID PERCENTAGE ON DIFFERENT ROOTSTOCKS

| Date | New Var. on Cleopatra Mandarin Rootstock | New Var. on Troyer Citrange Rootstock | New Var. on Trifoliate Rootstock | Frost Nucellar on Trifoliate | Atwood on Cleopatra |
|---|---|---|---|---|---|
| 10/16 | 1.49 | 1.53 | 1.43 | 1.55 | 1.78 |
| 10/30 | 1.22 | 1.31 | 1.47 | 1.32 | 1.04 |
| 11/13 | 1.08 | 1.24 | 1.18 | 1.29 | 1.59 |
| 11/26 | 1.01 | 1.20 | 1.20 | 1.18 | 1.25 |
| 12/10 | .93 | 1.21 | 1.22 | 1.15 | 1.17 |
| 12/31 | .94 | .99 | 1.04 | 1.08 | ---------- |

TABLE III.—SOLUBLE SOLIDS PERCENTAGE ON DIFFERENT ROOTSTOCKS

| Date | New Var. on Cleopatra Mandarin Rootstock | New Var. on Troyer Citrange Rootstock | New Var. on Trifoliate Rootstock | Frost Nucellar on Trifoliate | Atwood on Cleopatra |
|---|---|---|---|---|---|
| 10/16 | 9.4 | 10.7 | 9.9 | 9.3 | 10.3 |
| 10/30 | 11.1 | 11.7 | 11.2 | 8.7 | 8.1 |
| 11/13 | 9.6 | 11.0 | 10.5 | 10.6 | 11.6 |
| 11/26 | 10.1 | 11.6 | 11.0 | 10.5 | 11.1 |
| 12/10 | 10.4 | 11.6 | 11.6 | 10.5 | 10.9 |
| 12/31 | 10.1 | 11.6 | 11.6 | 10.6 | ---------- |

In these tables, my new variety grown on the different rootstocks Troyer Citrange, Cleopatra Mandarin, and Trifoliate, respectively, is compared with each other, as well as with the Atwood Navel on Cleopatra Mandarin and the Frost Nucellar Navel on Trifoliate, all unpatented. The Atwood Navel is a local early sport and the Frost Nucellar Navel is the popular strain of the Washington Navel which composes the major portion of recent orange plantings in central California.

My new variety is vegetatively very similar to its Washington Navel parent, and its fruit uniformity, relatively small navel size, good peel texture and quality are highly desirable. The common mutation dryness and navel or blossom end variability are absent in the new variety, and it is superior to any other early Washington Navel sport discovered up to the present time.

Due to the accelerated growth of the small fruit of the new variety, the fruit is approximately twice the size of the fruit of the traditional navel orange at the start of the hot season. For example, about the middle of May when the fruit size of the parent variety was ¼ inch in diameter, the fruit size of the new variety was ½ inch, and continuing in May and June, the fruit size comparison (expressed as the ratio of the new variety to the parent variety) were ¾ inch:½ inch on May 31, 1 inch:¾ inch on June 15, and 1½ inches:1 inch on June 30, with the fruit of the new variety continuing to consistently show a substantially larger size than the parent variety. This is a very desirable and important characteristic of the new variety because it tends to lessen the amount of so-called "June drop," which is an affliction of small deciduous fruit during the first hot days of the summer season when the fruit normally tends to wither, die and fall from the tree. The accelerated maturity results in larger and more mature fruit when this heat period arrives, thereby reducing the loss by drop. Extensive field tests have demonstrated excellent fruit crop production, while the tree vigor is considered normal.

I claim:

1. A new and distinct variety of navel orange tree, substantially as herein shown and described, characterized particularly as to novelty by the unique combination of foliage which is somewhat smaller than that of the Washington Navel parent, a habit of blooming profusely and setting fruit exceptionally well at an early age, usually beginning at one or two years of age when grown in the field, stout fruit stems which cause the fruit to remain more firmly attached to the tree than in the Washington Navel parent, rapid acceleration of the growth of the small fruit which usually becomes apparent during the month of May and early June in California, a habit of changing the fruit color from green to orange more rapidly than the Washington Navel parent, a fruit maturity ranging from 10 days to 3 weeks earlier than the Washington Navel variety in reaching the required sugar or soluble solids to acid ratio of 8:1, and excellent quality and flavor of the fruit comparable to the parent variety.

No references cited.

ROBERT E. BAGWILL, *Primary Examiner.*